United States Patent
Bruni et al.

(10) Patent No.: US 6,383,738 B1
(45) Date of Patent: May 7, 2002

(54) HERPES SIMPLEX VIRUS ORF P IS A REPRESSOR OF VIRAL PROTEIN SYNTHESIS

(75) Inventors: Renato Bruni; Bernard Roizman, both of Chicago, IL (US)

(73) Assignee: Arch Development Corporation, Chicago, IL (US)

(*) Notice: Subject to any disclaimer, the term of this patent is extended or adjusted under 35 U.S.C. 154(b) by 0 days.

(21) Appl. No.: 09/206,676

(22) Filed: Dec. 7, 1998

Related U.S. Application Data (62) Division of application No. 08/706,308, filed on Aug. 30, 1996, now Pat. No. 5,846,948.

(51) Int. Cl.$^7$ .................. A61K 39/245; C07H 21/04; C07K 14/03; C12N 5/16; C12N 7/00

(52) U.S. Cl. .................. 435/5; 424/186.1; 424/199.1; 424/229.1; 424/231.1; 435/69.1; 435/70.1; 435/71.1; 435/235.1; 435/236; 435/325; 435/320.1; 530/350; 514/44; 536/23.72; 536/24.1

(58) Field of Search .................. 424/184.1, 199.1, 424/229.1, 231.1; 435/69.1, 70.1, 71.1, 325, 320.1, 5, 235.1, 236; 530/350; 514/44; 536/23.72, 24.1

(56) References Cited

PUBLICATIONS

Orkin et al. Report and Recommendations of the Panel to Assess the NIH Investment in Research on Gene Therapy, Dec. 7, 1995.*
Coglan, New Scientist, Nov. 25, 1995, pp. 14–15.*
Carter and Roizman, "The Promoter an d Transcriptional Unit of a Novel Herpes Simplex Virus 1 α Gene are Contained in, and Encode a Protein in Frame with, the Open Reading Frame of the α22 Gene," *J Virology*, 70(1):172–178, Jan. 1996.
DeLuca et al., "Isolation and Characterization of Deletion Mutants of Herpes Simplex Virus Type 1 in the Gene Encoding Immediate–Early Regulatory Protein ICP4," *J Virology*, 56(2):558–570, Nov. 1985.
Fu, "The Superfamily of Arginine/Serine–Rich Splicing Factors," *RNA*, 1:663–680, 1995.
Glorioso et al., "Development and Application of Herpes Simplex Virus Vectors for Human Gene Therapy," *Annu rev Microbiol*, 49:675–710, 1995.
Honess and Roizman, "Regulation of Herpes Virus Macromolecular Synthesis. I. Cascade Regulation of the Synthesis of Three Groups of Viral Proteins," *J Virology*, 14(1):8–19, Jul. 1974.
Kanopka et al., "Inhibition by SR Proteins of Splicing of a Regulated Adenovirus Pre–mRNA," *Nature*, 381:535–538, Jun. 1996.

Lagunoff and Roizman, "The Regulation of Synthesis and Protein Product of Open Reading Frame P of the Herpes Simplex Virus 1 Genome," *J Virology*, 69(6):3615–3623, Jun. 1995.
Lagunoff et al., "Phenotypic Properties of Herpes Simplex Virus 1 Containing a Depressed Open Reading Frame P Gene," *J Virology*, 70(3):1810–1817, Mar. 1996.
McNally and McNally, "SR Protein Splicing Factors Interact with the Rous Sarcoma Virus Negative Regulator of Splicing Element," *J Virol*, 70(2):1163–1172, Feb. 1996.
Pettersson et al., "The Structure of Mammalian Small Nuclear Ribonucleoproteins," *J Biological Chemistry*, 259(5907–5914, May 1984.
Ward and Roizman, "*Herpes Simplex* Genes: The Blueprint of a Successful Human Pathogen," *Trends Genet*, 10(8):267–274, Aug. 1994.
Bruni and Roizman, "Open reading frame P–aherpes simplex virus gene repressed during productive infection encodes a protein that binds a slicing factor and reduces synthesis of viral proteins made from spliced mRNA," *Proc. Natl. Acad. Sci. USA*, 93:10423–10427, Sep. 1996.
International Search Report dated Dec. 19, 1997. (ARCD:241P).
Lagunoff and Roizman, "Expression of a herpes simplex virus 1 open reading frame antisense to the $\gamma_1 34.5$ gene and transcribed by an RNA 3'coterminal with the unspliced latency–associated transcript," *J. Virol.*, 68(9):6021–6028, Sep. 1994.
Gura, "Antisense has growing pains," *Science*, 270:575–577, 1995.
Harris et al., *TIBSTECH*, 11:42–44, 1993.
Miller et al., *Parasitology Today*, 10(3):92–97, 1994.
Rojanasakul, *Advanced Drug Delivery Reviews*, 18:115–131, 1996.
Stein et al., "Antisense oligonucleotides as therapeutic agents—is the bullet really magical?" *Science*, 261:1004–1012, 1993.
Stull et al., "Some characteristics of metabolism of organochlorine componds in the bovine," *Pharmaceutical Research*, 12(4):465–483, 1995.
Wagner et al., "Gene inhibition using antisense oligodeoxynucleotides," *Nature* 372:333–335, 1994.
Weiss et al., *Science News*, 139:108–109, 1991.
Wu Pong, *Pharmaceutical Technology*, 18:102–114, 1994.

* cited by examiner

Primary Examiner—Phuong T. Bui
(74) Attorney, Agent, or Firm—Fulbright & Jaworski, LLP (57) ABSTRACT

The present invention is directed to methods and compositions relating to the treatment of herpes simplex virus infections and the screening of compounds for activity that inhibit or promote viral latency. The previously identified ORF P gene product now has been shown to interact with certain eukaryotic splicing factors and, in a cell infected with a herpesvirus containing a derepressed ORF P gene, ORF P can limit the splicing of at least two viral products. Given this function, it now is possible to screen for inhibitors and inducers of ORF P and, further, provide methods for maintaining and preventing viral latency.

14 Claims, 3 Drawing Sheets

HERPES SIMPLEX VIRUS ORF P IS A REPRESSOR OF VIRAL PROTEIN SYNTHESIS

This is a divisional of application Ser. No. 08/706,308 filed Aug. 30, 1996, now U.S. Pat. No. 5,846,948.

The government may own certain rights in this application by virtue of federal funding under grant numbers AI124009 (NIAID) and CA47451 (NCI).

BACKGROUND OF THE INVENTION

I. Field of the Invention

The present invention relates to the fields of molecular and cell biology generally, and more specifically, it addresses mechanisms for growth control in eurkaryotic cells. In particular, there are provided viral genes that inhibit viral protein synthesis and methods for use thereof.

II. Related Art

Herpes simplex viruses, designated with subtypes 1 and 2, are enveloped viruses that are among the most common infectious agents encountered by humans, infecting millions of human subjects worldwide. These viruses cause a broad spectrum of disease which ranges from relatively insignificant to severe and life-threatening. Clinical outcome of herpes infections is dependent upon early diagnosis and prompt initiation of antiviral therapy. Despite some successful efforts in treating HSV infectious, dermal and epidermal lesion often recur, and HSV infections of neonates and infections of the brain are associated with high morbidity and mortality.

Herpes simplex virus 1 (HSV-1) causes two kinds of infection. The first, exemplified most dramatically after first exposure to the virus, results in productive infection at the portal of entry of the virus into the body. In productive infection, approximately 80 different genes are expressed, viral protein and DNA are made, viral progeny is assembled and, ultimately, the cell is destroyed. The second type of infection, latent infection, takes place only in sensory neurons populated by viruses brought to that sites by retrograde transport along axons from the portal of entry. In latently infected cells, viral DNA is maintained as an episome, and the only products detected to date are transcripts arising from two copies of a 8.5 kB domain of the DNA. Recombinants lacking sequences encoding the promoters and 5' domains of these RNAs, however, are capable of establishing latent infections. These finding suggested that either as yet unknown viral gene products or cellular gene products are responsible for the establishment of the latent state (Roizman and Sears, 1995).

The genes expressed during the productive infection encode numerous functions related not only to viral replication, but also to the increase of the pool of susceptible cells, to more efficient spread of infection from cell to cell and to the abrogation of host response to infection (Ward and Roizman, 1994). In light of these specialized activities, it is rather unlikely that establishment of latency, a vital function for the perpetuation of the virus in human populations, would solely rely on functions expressed by the host cell. Experiments designed to look for viral genes expressed during latency led to the discovery that an open reading frame, designated as ORF P, is repressed during productive infection, but is expressed under conditions where the repressor is not made or the site of binding of the repressor is ablated (Lagunoff & Roizman, 1994; 1995). A definite functional link between this gene product and latency has not been established.

SUMMARY OF THE INVENTION

It is, therefore, an object of the present invention to provide methods for the treatment of HSV infections, and compositions therefor. More specifically, it is an object of the present invention to provide methods that inhibit, induce or maintain latency of herpesvirus infections. It also is an object of the present invention to provide methods for the identification of compositions that will inhibit, induce or maintain latency of HSV infections.

In satisfying these objectives, there is provided, in a first embodiment, a method for inducing latency in a herpesvirus infected cell comprising the step of increasing the level of ORF P polypeptide in the cell. The herpesvirus may be a herpes simplex virus and, more particularly, a type 1 herpes simplex virus or a type II herpes simplex virus. The cell may be a human cell and, in a preferred embodiment, a human cell located in a human subject.

Increasing the level of ORF P may comprise providing an ORF P polypeptide to the cell, for example, by contacting the cell with an ORF P polypeptide. Alternatively, providing may comprise contacting the cell with a nucleic acid encoding an ORF P polypeptide. Preferably, the nucleic acid is under the transcriptional control of a promoter active in eukaryotic cells, for example, a herpesvirus promoter. The nucleic acid may further be contained in a replication-deficient vector, such as a replication-deficient herpesvirus vector. The herpesvirus vector may be contained in an infectious herpesvirus particle, where contacting is performed under conditions that permit infection of the cell by the herpesvirus particle. This method may further comprise a step of administering an anti-viral agent to the cell.

In another embodiment, there is provided a method for preventing latency in a herpesvirus infected cell comprising the step of decreasing the level of ORF P polypeptide in the cell. The herpesvirus may be a herpes simplex virus and, more particularly, a type 1 herpes simplex virus or a type II herpes simplex virus. The cell may be a human cell and, in a preferred embodiment, a human cell located in a human subject. Decreasing ORF P may comprise providing to the cell an antisense construct, wherein the antisense construct inhibits transcription or translation of an ORF P gene. The antisense construct may comprise an oligonucleotide that targets a 5'-untranslated region or a translational start site for ORF P. Alternatively, decreasing may comprise inhibiting translational processing of the ORF P polypeptide. In another alternative, decreasing may comprise providing to the cell an antibody that binds immunologically to the ORF P polypeptide. Preferably, the antibody is a monoclonal antibody.

In still another embodiment, there is provided a method for inhibiting the splicing of a RNA transcript comprising the step of contacting the transcript with an ORF P polypeptide. The RNA transcript may be produced in an in vitro transcription system or it may be produced in a cell. The ORF P is produced recombinantly and it may be produced in the same cell as the RNA transcript. The recombinant ORF P may be under the control of an inducible promoter.

In still yet another embodiment, there is provided a method for isolating a splicing factor comprising the steps of (a) providing an ORF P polypeptide; (b) contacting the ORF P polypeptide with a cell extract containing a splicing factor; and (c) isolating the ORF P polypeptide-splicing factor complex. Preferably, the ORF P polypeptide is bound to a support.

In still yet a further embodiment, there is provided a method for isolating an SM antigen comprising the steps of (a) providing an ORF P polypeptide; (b) contacting the ORF P polypeptide with a cell extract containing an SM antigen; and (c) isolating the ORF P polypeptide-SM antigen complex. Preferably, the ORF P polypeptide is bound to a support Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A–B: Schematic representation of the sequence arrangement of the HSV-1 genome and of the location and polarity of the ORF P gene.

DETAILED DESCRIPTION OF THE INVENTION

HSV-1 has a large, complex, double-stranded DNA genome that encodes >80 different gene products, a few of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975; Roizman and Sears, 1995). The expression of α genes, the first set of genes to be expressed after infection, is enhanced by the virion protein number 16, or α-transinducing factor (post et al., 1981; Batterson and Roizman, 1983; Campbell, et al., 1984). The expression of β genes requires functional α gene products, most notably ICP4, which is encoded by the α4 gene (DeLuca et al., 1985). γ genes, a heterogeneous group of genes encoding largely virion structural proteins, require the onset of viral DNA synthesis for optimal expression (Honess & Roizman, 1975; Holland et al., 1980).

In line with the complexity reflected by the viral genome, the life cycle of HSV is quite involved as well. In addition to the lytic cycle, which results in synthesis of virus particles and, eventually, cell death, the virus has the capability to enter a latent state. Sensory neurons are populated by viruses brought to that site by retrograde transport along axons from the portal of entry. The genome is maintained in neural ganglia until some signal triggers a recurrence of the lytic cycle. In latently infected cells, viral DNA is maintained as an episome, and the only products detected to date are transcripts arising from two copies of a 8.5 kB domain of the DNA. Recombinants lacking sequences encoding the promoters and 5' domains of these RNAs, however, are capable of establishing latent infections. A previous study has determined that an open reading frame in this region, designated ORF P, encodes a polypeptide that can be produced in cells infected with a certain kind of mutant virus (Lagunoff and Roizman, 1995). It has yet to be established that this protein is actually synthesized in a latently infected neuron.

According to the present invention, it now has been determined that, in cells infected with a mutant virus carrying a derepressed ORF P, (i) ORF P protein interacts with and colocalizes with splicing factors, and (ii) the accumulation of ICP0 and ICP22, two regulatory proteins made from spliced mRNAs, is reduced early in infection but recovers late in infection, particularly in cells in which ORF P protein is post-translationally modified. More specifically, ORF P interacts with a component of the splicing factor SF2/ASF, coprecipitates a component of the SM antigens and colocalizes with splicing factors in the nucleic of infected cells. In at least two cases, this interaction apparently leads to the reduction of HSV proteins. Thus, it is believed that the inhibition of viral protein synthesis mediated by ORF P occurs at a post-transcriptional level, and likely involves splicing of viral mRNA.

The splicing factor SF2/ASF belongs to the growing family of SR proteins (Fu, 1995). SR proteins are essential splicing factors and are also involved in the selection of alternative splice sites (Cáceres et al., 1994; Wang and Manley, 1995). Interestingly, two SR proteins, SF2/ASF and SC35, have been shown to play a role in the repression of splicing of certain viral mRNAs (Kanopka et al., 1996; McNally and McNally, 1996). Thus, ORF P's interaction with SF2/ASF, or with SR proteins in general, likely interferes with or disturbs the activity of spliceosomes. HSV encodes only four genes known to yield spliced mRNAs. These include three α—genes α0, α22, and α47—and the late or γ gene $U_L15$. The introns of α22 and α47 are located within identical inverted repeats and therefore the splice donor and acceptor sites should be identical.

In the examples set forth below, it is demonstrated that, in cells infected with a mutant HSV carrying the derepressed ORF P, the amounts of ICP22 and ICP0 are reduced relative to those amounts accumulating in wild-type virus-infected cells. It also is shown that the levels of ICP4 and ICP27, the products of α genes which yield non-spliced mRNAs, are unaffected by ORF P. Lastly, it is shown that, late in infection, the levels of ICP22 and ICP0 recover and approach those of wild-type infected cells. The extent of recovery, however, correlates with the accumulation of post-translationally modified ORF P protein.

The results of these studies indicate tat ORF P can repress the expression of at least two viral regulatory genes, and by extension, can repress productive infection, a process essential for the establishment of latency. It should be noted that ORF P may not be the sole factor involved in establishment of latency inasmuch as viruses lacking ORF P are capable of establishing latent infections, albeit at a reduced rate. An interesting property of HSV is that other key functions such as entry into cells, regulation of gene expression, viral DNA synthesis, packaging of viral DNA into capsids and egress from infected cells all involve several gene products (Roizman and Sears, 1995; Ward and Roizran, 1994). Therefore, it would not be surprising if additional viral and cellular genes, some as of yet unknown, also are found to play a role in the establishment of latent infections.

I. ORF P

Figure 1A:
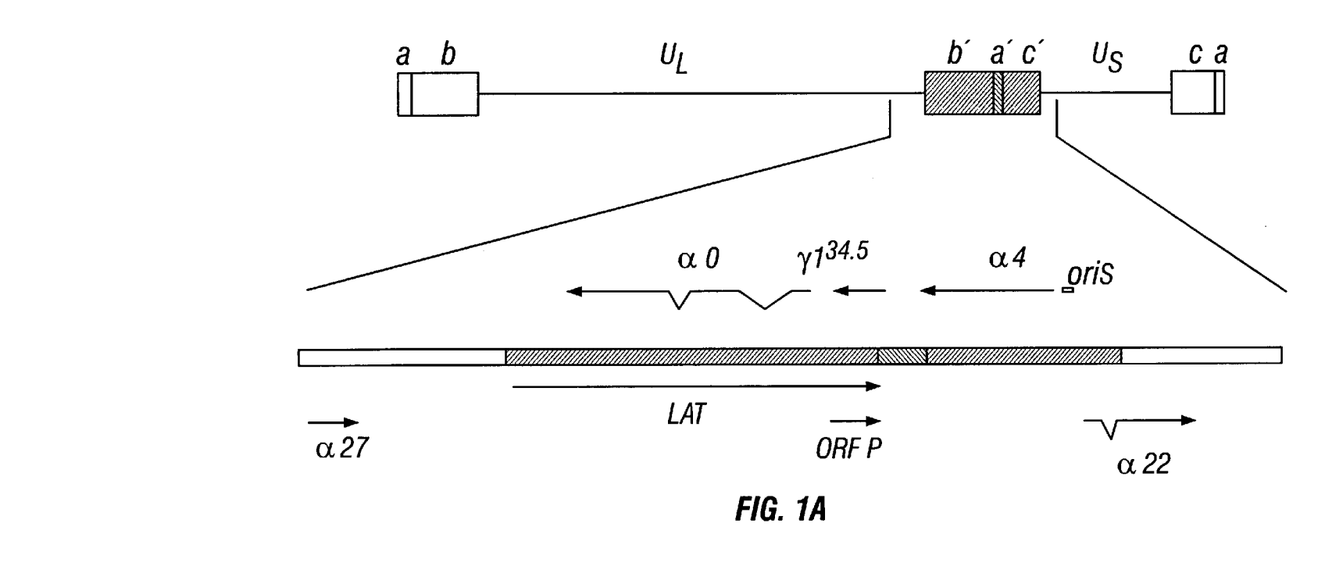
FIG. 1A. Top line: representation of the HSV-1 genome. Thin lines represent the unique long ($U_L$) and unique short ($U_S$) sequences. The rectangles represent the inverted repeats sequences ab and b'a' flanking $U_L$ and a'c' and ca flanking $U_S$. Bottom line: expanded section of the internal inverted repeat and adjacent sequences. Shown are genes relevant for these studies. ORF P is almost completely antisense to the $\gamma_1 34.5$ gene and maps in the b sequence of the inverted repeats.

ORF P is encoded by an open reading frame located in the inverted repeats flanking the unique long ($U_L$) sequences of HSV DNA antisense to a gene designated $γ_134.5$ (see FIG. 1A). The transcription initiation site of ORF P coincides with the location of a high affinity binding site of infected cell protein No. 4 (ICP4) (Lagunoff & Roizman, 1994; 1995). This protein functions as a transactivator of many viral genes, but as a repressor of the ORF P-encoding transcript (Roizman and Sears, 1995). This repression is particularly strong, as evidenced by the observation that the products of the ORF P are observed only under conditions in which ICP4 is not functional or when its binding site at the transcription initiation site of the ORF P is ablated by mutagenesis (Lagunoff & Roizman, 1994; 1995).

Figure 1B:
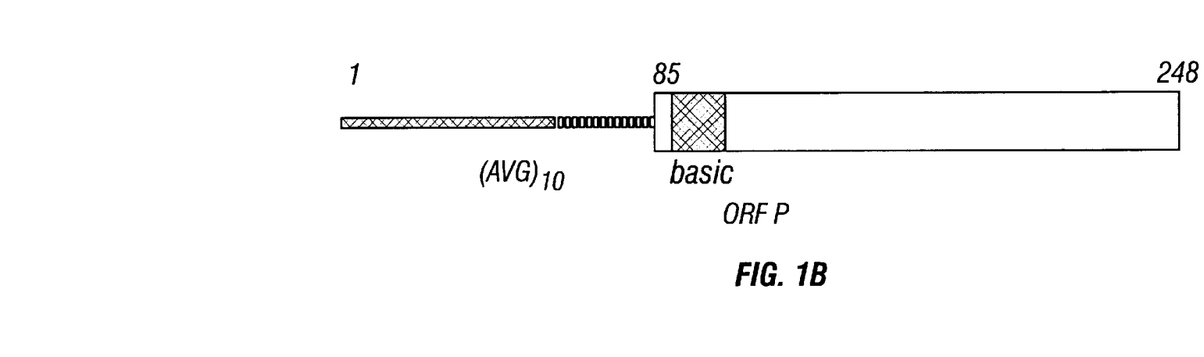
FIG. 1B. The domains of the ORF P protein consisting of a aminoterminal domain (black line), 3 amino acids (alanine-glycine-valine) repeated 10 times (striped line), a short basic domain, followed by a longer carboxyl terminal domain. The stippled box is the region used in the two hybrid system.

ORF P expressed by HSV-1 strain F is predicted to contain 248 amino acids. Inasmuch as it is almost entirely antisense to the $γ_134.5$ gene, it contains a short amino terminal domain, followed by 3 amino acids repeated 10 times, and a long carboxyl terminal domain (see FIG. 1B). In Vero cells infected with viruses carrying a derepressed ORF P, the nascent protein designated ORF Pa is post-translationally processed to slower migrating forms ORF Pb and ORF Pc, and late in infection the protein appears to aggregate into dense structures which do not colocalize with the sites of viral DNA synthesis or late gene transcription. These observations led to the suggestion that the post-translational processing of ORF P inactivates its function (Lagunoff & Roizman, 1995).

In referring to ORF P "activity" or "function," it is meant that ORF P decreases viral polypeptide synthesis. This activity or function may be via inhibition of mMRNA splicing, but may be via other mechanisms as well, or as alternative thereto. Reference to "wild-type ORF P" indicates the ORF P of SEQ ID NO:1. ORF P function is not believed dependent on wild-type ORF P.

ORF P may be obtained according to various standard methodologies that are known to those of skill in the art. For example, antibodies specific for ORF P may be used in immunoaffinity protocols to isolate ORF P from infected cells, in particular, from cell lysates of cells infected with a mutant that contains a derepressed ORF P gene (Lagunoff & Roizman, 1995). Antibodies are advantageously bound to supports, such as columns or beads, and the immobilized antibodies can be used to pull the ORF P target out of the cell lysate.

Alternatively, expression vectors, rather than HSV infections, may be used to generate ORF P. A wide variety of expression vectors may be used, including other types of viral vectors. The structure and use of these vectors is discussed further, below. Such vectors may significantly increase the amount of ORF P protein in the cells, and may permit less selective purification methods such as size fractionation (chromatography, centrifugation), ion exchange or affinity chromatograph, and even gel purification.

ORF P, according to the present invention, may advantageously be cleaved into fragments for use in further structural or functional analysis, or in the generation of reagents such as ORF P-related polypeptides and ORF P-specific antibodies. This can be accomplished by treating purified or unpurified ORF P with a peptidase such as endoproteinase glu-C (Boehringer, Indianapolis, Ind.). Treatment with CNBr is another method by which ORF P fragments may be produced from natural ORF P. Recombinant techniques also can be used to produce specific fragments of ORF P.

It is expected that changes may be made in the sequence of ORF P while retaining a molecule having the structure and function of wild-type ORF P. For example, certain amino acids may be substituted for other amino acids in a protein structure without appreciable loss of interactive capacity with structures such as, for example, substrate-binding regions. These changes are termed "conservative" in the sense that they preserve the structural and, presumably, required functional qualities of the starting molecule. Variants of this nature may be screened by any of the functional assays provided in the examples.

Conservative amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as equivalent.

In making such changes, the hydropathic index of amino acids also may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity, particularly where the polypeptide created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

Numerous scientific publications have been devoted to the prediction of secondary structure, and to the identification of epitopes, from analyses of amino acid sequences (Chou & Fasman, 74a,b; 1978a,b; 1979). Any of these may be used, if desired, to supplement the teachings of Hopp in U.S. Pat. No. 4,554,101. Moreover, computer programs are currently available to assist with predicting antigenic portions and epitopic core regions of proteins. Examples include those programs based upon the Jameson-Wolf analysis (Jameson & Wolf, 1998; Wolf et al., 1988), the program PepPlot® (Brutlag et al., 1990; Weinberger et al., 1985), and other new programs for protein tertiary structure prediction (Fetrow & Bryant, 1993).

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate= Glu (E); Glutamine=Gln (Q); Glycine=Gly (G); Histidine= His (H); Isoleucine=Ile (I); Leucine=Leu (L); Lysine=Lys (K); Methionine=Met (M); Phenylalanine=Phe (F); Proline= Pro (P); Serine=Ser (S); Threonine=Thr (T); Tryptophan= Trp (W); Tyrosine=Tyr (Y); Valine=Val (V).

In addition to the peptidyl compounds described herein, the inventors also contemplate that other sterically similar compounds may be formulated to mimic the key portions of the peptide structure, called peptidomimetics. Mimetics are peptide-containing molecules which minmic elements of protein secondary structure. See, for example, Johnson et al. (1993). The underlying rationale behind the use of peptide mimetics is that the peptide backbone of proteins exists chiefly to orient amino acid side chains in such a way as to facilitate molecular interactions, such as those of receptor and ligand.

Successful applications of the peptide mimetic concept have thus far focused on mimetics of β-turns within proteins. Likely β-turn structures within ORF P can be predicted by computer-based algorithms as discussed above. Once the component amino acids of the turn are determined, mimetics can be constructed to achieve a similar spatial orientation of the essential elements of the amino acid side chains, as discussed in Johnson et al. (1993).

III. Nucleic Acids Encoding ORF P

Also contemplated by the present invention are nucleic acids encoding ORF P. The wild-type gene for ORF P is provided herein as SEQ ID NO:2. Because of the degeneracy of the genetic code, many other nucleic acids also may encode a given ORF P. For example, four different three-based codons encode the amino acids alanine, glycine, proline, threonine and valine, while six different codons encode arginine, leucine and serine. Only methionine and tryptophan are encoded by a single codon. A table of amino acids and the corresponding codons is presented herein for use in such embodiments.

TABLE 1

| Amino Acids | | | Codons |
|---|---|---|---|
| Alamine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In order to generate any nucleic acid encoding ORF P, one need only refer to the preceding codon table. Substitution of the natural codon with any codon encoding the same amino acid will result in a distinct nucleic acid that encodes ORF P. As a practical matter, this can be accomplished by site-directed mutagenesis of an existing ORF P gene or de novo chemical synthesis of one or more nucleic acids.

The preceding observations regarding codon selection, site-directed mutagenesis and chemical synthesis apply with equal force to the discussion of substitutional mutants in the section of peptides. Normally, substitutional mutants are generated by site-directed changes in the nucleic acid designed to alter one or more codons of the coding sequence.

In order to express an ORF P polypeptide, or an ORF P transcript (discussed below), it is necessary to provide an ORF P gene in an expression vector. Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product.

The appropriate nucleic acid can be inserted into an expression vector by standard subcloning techniques. For example, an E. coli or baculovirus expression vector or viral expression vector is cleaved and an ORF P nucleic acid is inserted therein in vitro. The manipulation of these vectors is well known in the art. Selection of appropriate restriction enzymes, based on the availability of useful restriction sites, will be based on the skilled artisan's judgment. Alteration of the nucleic acid to create novel restriction sites without changing the amino acid sequence may be accomplished by site-directed mutagenesis.

In one embodiment, the protein is expressed as a fusion protein with β-gal, allowing rapid affinity purification of the protein. Examples of such fusion protein expression systems are the glutathione S-transferase system (Pharmacy, Piscataway, N.J.), the maltose binding protein system (NEB, Beverley, Mass.), the FLAG system (IBI, New Haven, Conn.), and the 6×His system (Qiagen, Chatsworth, Calif.). Some of these fusion systems produce recombinant protein bearing only a small number of additional amino acids, which are unlikely to affect the functional capacity of the recombinant protein. For example, both the FLAG system and the 6×His system add only short sequences, both of which are known to be poorly antigenic and which do not adversely affect folding of the protein to its native conformation. Other fusion systems produce proteins where it is desirable to excise the fusion partner from the desired protein. In another embodiment, the fusion partner is linked to the recombinant protein by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

Recombinant bacterial cells, for example E. coli, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents such as β-mercaptoethanol or DTT (dithiothreitol).

Under some circumstances, it may be advantageous to incubate the polypeptide for several hours under conditions suitable for the protein to undergo a refolding process into a conformation which more closely resembles that of the native protein. Such conditions generally include low protein concentrations less than 500 μg/ml, low levels of reducing agent, concentrations of urea less than 2 M and often the presence of reagents such as a mixture of reduced and oxidized glutathione which facilitate the interchange of disulphide bonds within the protein molecule.

The refolding process can be monitored, for example, by SDS-PAGE or with antibodies which are specific for the native molecule (which can be obtained from animals vaccinated with the native molecule isolated from parasites). Following refolding, the protein can then be purified further and separated from the refolding mixture by chromatography on any of several supports including ion exchange resins, gel permeation resins or on a variety of affinity columns.

In yet another embodiment, the expression system used is one driven by the baculovirus polyhedron promoter. The gene encoding the protein can be manipulated by standard techniques in order to facilitate cloning into the baculovirus vector. A preferred baculovirus vector is the pBlueBac vector (Invitrogen, Sorrento, Calif.). The vector carrying the α4 gene is transfected into Spodoptera frugiperda (e.g., Sf9) cells by standard protocols, and the cells are cultured and processed to produce the recombinant protein.

There also are a variety of eukaryotic vectors that provide a suitable vehicle in which recombinant ORF P can be produced. This system provides many advantages, for example, a better opportunity for normal post translation processing. This also permits genetic therapy of living eukaryotic cells. In various embodiments of the invention, the expression construct may comprise a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) and adeno-associated virus (Ridgeway, 1988). Such vectors may be used to (i) transform cell lines in vitro for the purpose of expressing proteins of interest or (ii) to transform cells in vitro or in vivo to provide therapeutic polypeptides in a gene therapy scenario.

In a preferred embodiment, the vector is HSV. Because HSV is neurotropic, it can effectively target the same cells which harbor natural HSV—neural ganglia. Thus, where the purpose of the invention is to treat latently infected cells, the ability of HSV to target neuronal cells is highly advantageous. And though much attention has focused on the neurotropic applications of HSV, this vector also can be exploited for other tissues, i.e., tissues undergoing primary, acute infection.

Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. Obviously, depending on the particular application, the vector used may employ modified viral products that are no longer spliced and/or it may contain a deregulated ORF P gene or a non-functional ORF P product.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al., 1995.

In an alternative embodiment, the ORF P nucleic acids employed may actually encode antisense constructs that hybridize, under intracellular conditions, to an ORF P nucleic acid. The term "antisense construct" is intended to refer to nucleic acids, preferably oligonucleotides, that are complementary to the base sequences of a target DNA or RNA. Antisense oligonucleotides, when introduced into a target cell, specifically bind to their target nucleic acid and interfere with transcription, RNA processing, transport, translation and/or stability.

Antisense constructs may be designed to bind to the promoter and other control regions, exons, introns or even exon-intron boundaries of a gene. Antisense RNA constructs, or DNA encoding such antisense RNA's, may be employed to inhibit gene transcription or translation or both within a host cell, either in vitro or in vivo, such as within a host animal, including a human subject. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As used herein, the term "complementary" means nucleic acid sequences that are substantially complementary over their entire length and have very few base mismatches. For example, nucleic acid sequences of fifteen bases in length may be termed complementary when they have a complementary nucleotide at thirteen or fourteen positions with only a single mismatch. Naturally, nucleic acid sequences which are "completely complementary" will be nucleic acid sequences which are entirely complementary throughout their entire length and have no base mismatches.

Other sequences with lower degrees of homology also are contemplated. For example, an antisense construct which has limited regions of high homology, but also contains a non-homologous region (eg., a ribozyme) could be designed. These molecules, though having less than 50% homology, would bind to target sequences under appropriate conditions.

While all or part of the ORF P gene sequence may be employed in the context of antisense construction, short oligonucleotides are easier to make and increase in vivo accessibility. However, both binding affinity and sequence specificity of an antisense oligonucleotide to its complementary target increases with increasing length. It is contemplated that antisense oligonucleotides of 8, 9, 10, 11, 12, 13, 14, 15, 16, 17, 18, 19, 20, 25, 30, 35, 40, 45, 50, 60, 70, 80, 90, 100 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

In preferred embodiments, the nucleic acid of the expression construct is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modulus that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a nucleic acid is not believed to be critical, so long as it is capable of expressing the nucleic acid in the targeted cell under the appropriate circumstances. Thus, where a human cell is targeted, it is preferable to position the nucleic acid coding region adjacent to and under the control of a promoter that is capable of being expressed in that particular human cell. Generally speaking, such a promoter might include either a human or viral promoter. Preferred promoters include those derived from HSV In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Tables 2 and 3 list several elements/promoters which may be employed, in the context of the present invention, to regulate the expression of a transgene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 2

PROMOTER

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MRC Class II HLA-DRα
β-Actin
Muscle Creatine Kinase
Prealbumin (Transthyretin)
Elastase I
Metallotbionein
Collagenase
Albumin Gene
α-Fetoprotein
τ-Globin
β-Globin
c-fos
c-HA-ras
Insulin
Neural Cell Adhesion Molecule (NCAM)
$α_{1\text{-Antitrypsin}}$
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegaloviuus
Gibbon Ape Leukemia Virus

TABLE 3

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X |
| | poly(rc) |
| Adenovinis 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-ThA |
| Tumor Necrosis Factor | FMA |
| Thyroid Stimulating Hormone α Gene | Thyroid Hormone |

One will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements (Bittner et al., 1987).

IV. Methods for the Induction of Viral Replication

In another embodiment of the present invention, there is contemplated a method of inducing viral replication in HSV latently-infected cells by blocking the function of ORF P. In this way, it may be possible to eliminate viral infections by forcing the virus out of, or preventing entry into, its latent state. This approach may prove particularly effective in combination with more traditional chemotherapies, such as the administration of acyclovir.

The general form that this aspect of the invention will take is the provision, to a cell, of an agent that will inhibit ORF P function. Five such agents are contemplated. First, one may employ an antisense nucleic acid that will hybridize either to the ORF P gene or the ORF P transcript, thereby preventing transcription or translation, respectively. The considerations relevant to the design of antisense constructs have been presented above. Second, one may utilize an ORF P-binding protein or peptide, for example, a peptidomimetic or an antibody that binds immunologically to an ORF P, the binding of either will block or reduce the activity of an ORF P merely by providing a steric hindrance to the interaction of ORF P and its target. The methods of making or identifying peptide binding partners and antibodies are well known to those of skill in the art. Third, one may provide to the cell an antagonist of ORF P, for example, the ORF P target molecule, alone or coupled to another agent. Fourth, one may provide an agent that binds to the ORF P target without the same functional result as would arise with ORF P binding. And fifth, one may employ an agent that increases the post-translational processing of ORF P to its inactive form, for example, increasing the amount of an enzyme that phosphorylates or otherwise processes ORF P. Through the remainder of this section, all of these molecules will be referred to as "inhibitory agents." The utility of such agents may be ascertained by the screening methods described in following sections.

Provision of an inhibitory agent would be according to any appropriate pharmaceutical route, although topical routes are particularly contemplated. The formulation of such compositions and their delivery to tissues is discussed below. The method by which the nucleic acid, protein or chemical is transferred, along with the preferred delivery route, will be selected based on the particular site to be treated. Those of skill in the art are capable of determining the most appropriate methods based on the relevant clinical considerations.

With respect to gene transfer particularly, many of the techniques that generally are applied in vitro can be adapted for in vivo use. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988). In one embodiment of the invention, the expression vector may simply consist of naked recombinant expression vector.

Transfer of an expression construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif(1986) also demonstrated that direct intraperitoneal injection of $CaPO_4$ precipitated plasmids results in expression of the transfected genes. It is envisioned that DNA encoding an ORF P antisense cassette may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ. DNA encoding an ORF P antisense construct may be delivered via this method.

In a further embodiment of the invention, the inhibitory agent may be entrapped in a liposome. Liposomes are vesicular structures characterized by a phospholipid bilayer membrane and an inner aqueous medium. Multilamellar liposomes have multiple lipid layers separated by aqueous medium. Liposomes form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). In one embodiment, there is contemplated a lipofectamine-DNA complex.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacteriophage promoter is employed in the DNA construct, it also will be desirable to include within the liposome an appropriate bacteriophage polymerase. This work with gene transfer suggests transfer of proteins by a similar mechanism.

Another mechanism for transferring expression vectors and proteins into cells is receptor-mediated delivery. This approach takes advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that an expression vector also may be specifically delivered into a cell type by any number of receptor-ligand systems, with or without liposomes. For example, epidermal growth factor (EGF) may be used as the receptor for mediated delivery of a DNA construct in cells that exhibit EGF receptor. Mannose can be used to target the mannose receptor on liver cells. Also, antibodies to viral proteins may be employed as targeting moieties.

Liposomes also present a suitable mode for transporting proteins into cells. Those of skill in the art are aware of how to modify liposome synthesis methodology to incorporate polypeptides thereinto.

Where the embodiment involves the use of an antibody that binds immiounologically to an ORF P polypeptide, consideration must be given to the mechanism by which the antibody is introduced into the cell cytoplasm. As stated above, this can be accomplished by simply contacting the antibody with the tissue in question or by encapsulating the antibody in a liposome.

Alternatively, this can be accomplished by providing an expression construct that encodes a single-chain antibody version of the antibody to be provided. Most of the discussion above relating to expression constructs for antisense versions of ORF P genes will be relevant to this aspect of the invention. Alternatively, it is possible to present a bifunctional antibody, where one antigen binding arm of the antibody recognizes an ORF P polypeptide and the other antigen binding arm recognizes a receptor on the surface of the cell to be targeted. Examples of suitable receptors would be an HSV glycoprotein such as gB, gC, gD or gH. In addition, it may be possible to exploit the Fc-binding function associated with HSV gE, thereby obviating the need to sacrifice one arm of the antibody for purposes of cell targeting.

Advantageously, one may combine any of the above-mentioned approaches with more conventional chemotherapeutic options. The dug acyclovir is active against HSV-1 and HSV-2. The drug inhibits actively replicating herpes virus but is not active against latent virus. Acyclovir is available in three formulations. For topical use, a five percent ointment produces therapeutic drug levels in mucocutaneous lesions. For systemic use, acyclovir may be administered orally or intravenously. The usual intravenous dosage in adults with normal renal function is 5 mg/kg infused at a constant rate over one hour and given every eight hours; this dosage produces peak plasma levels at about 10 g/ml. For HSV encephalitis, twice this dose is used. The usual adult oral dosage is 200 mg, five times daily, which produces plasma levels that are less than 10% as high as those achieved with intravenous administration; even these levels are inhibitory to the virus, however. Acyclovir is given in an oral dosage of 800 mg five times daily for the treatment of herpes zoster, although oral administration generally is reserved for patients with severe symptoms. A three percent opthalmic preparation produces inhibitory drug levels in the aqueous humor and is effective for herpes keratitis.

Perhaps the biggest challenge in inducing viral replication is targeting the cell of interest. In many situations, the cell will be a neuronal cell which harbors latent virus. Systemic administration of an agent may suffice if (i) that agent is transported, in sufficient levels, to neurons and (ii) the toxicity to non-neuronal cells and uninfected neuronal cells is sufficiently low. Alternatively, specifically targeting infected neuronal cells may alleviate systemic toxicity problems, but it is likely that infected cells can be distinguished from uninfected cells only using a few very specific protocols. Given ORF P's interaction with splicing factors that are present in normal cells, toxicity must be considered in developing a strategy. Where an acutely infected cell is targeted, for example, to prevent the establishment of a latent state, the toxicity concerns will be lessened as the ultimate death of such a cell would be inconsequential and, in any event, inevitable.

V. Methods for the Inhibition of Viral Replication

In another embodiment of the present invention, there are provided methods for the inhibition of HSV replication. Thus, the aim here will be to suppress viral infection, i.e., to prevent activation of the virus from its latent state or to curtail an active infection, possibly forcing the virus to assume a latent state, and possibly preventing latent infection by disturbing the natural viral life cycle. One way in which this problem will be approached is by increasing the concentration of ORF P inside infected cells. This may be accomplished by providing ORF P polypeptides or ORF P genes to a target cell. Also contemplated in this aspect of the invention is the stimulation of endogenous viral ORF P expression, or stabilization of virally-expressed ORF P polypeptide, e.g., the inhibition of ORF P phosphorylation or other post-translational processing. This may result in the prevention of latency, or it may not, but the benefits of limiting an acute infection are manifest—elimination of pain, discomfort and possible transmission of disease resulting from acute infection. In addition, maintenance of latent infections (blocking of recurrence) will prevent further active infections.

Transfer of ORF P protein or genes encoding ORF P will be accomplished as described for the "agents" of the preceding section. Similarly, agents that stabilize or enhance the level of ORF P in a target cell will be administered as standard pharmaceuticals, as described elsewhere in this document. Such agents may include inhibitors of the enzymes that process ORF P from its full length form to its proteolytically processed forms, or any other agents identified according to the screening assays described below. And again, it may be desirable to combine such treatments with standard chemotherapeutic approaches, such as administration of acyclovir.

VI. Methods for Screening of Active Compounds

A. Inhibitors of ORF P Activity

In one embodiment of the present invention, there are provided methods of screening compounds for activity against ORF P's protein synthesis inhibiting activity. As described previously, such compounds may be useful in treatments whereby latent infections are cured following induction and whereby latent infections are prevented in the first instance. These screening methods will determine either the blocking of ORF P's inhibition of protein synthesis or, more specifically, the blocking of ORF P's interaction with splicing functions. At least 3 different assays may be employed, as discussed below.

First, one may infect cells with a virus encoding a derepressed ORF P gene. As stated above, this virus will show initial low levels of ICP0 and ICP22, although later in infection, the levels will rise to those seen in wild-type infections. Monitoring of ICP0 and ICP22 levels during the early phases of infection, both in the presence and absence of a candidate inhibitor, will provide a way of measuring the inhibitory effect of the candidate.

Second, one may perform binding studies between ORF P and the various splicing factors which have been identified as targets for ORF P binding, may be examined when combined with ORF P and a candidate inhibitor. These assays may examine the mobility shift, in gel electrophoresis, of either ORF P or the splicing factor, both in the presence and absence of a candidate inhibitor.

Third, where the candidate inhibitor is predicted to reduce the amount of ORF P expressed, or to alter the processing of ORF P, one may look directly at ORF P in its various forms. Typically, the examination of ORF P will be on the basis of immunologic reactivity. This can be accomplished in a variety of ways but, advantageously will be performed via radioimmune precipitation, Western blot or other such routine assay.

It also has been observed that highly phosphorylated ORF P, presumably non-functional, aggregates into rods in the nucleus. In contrast, the non-phosphorylated ORF P colocalizes with splicing factors in spliceosomes. As a result, this differential subcellular localization can be determined by fluorescence microscopy. Depending on the specific mechanism of the inhibitor's action, one may look directly at phosphorylation of ORF P.

In many of these assays, the most convenient way to measure the effect of the candidate inhibitor will be to contact the inhibitor with an intact cell expressing ORF P and any other component necessary for the measurement. A preferred embodiment is one where the cell has been infected with a deregulated ORF P gene. In such cases, the cell may be contacted with the candidate inhibitor before, at the same time, or after contacting with the virus.

In some cases, the candidate inhibitor substance may be contacted with the cell directly. In other situations, depending on the nature and putative mechanism of action, the candidate inhibitor substance may be reformulated to provide improved uptake. For example, where antisense oligonucleotides are provided, these may advantageously be formulated in liposomes or as virally-encapsulated expression vehicles. Where polypeptides are to be tested, it may be advantageous to provide expression vectors encoding these molecules rather than the polypeptides themselves. Essentially, the most reasonable mechanism for delivering an effective amount of the candidate inhibitor substance to the proper intracellular site will be chosen. "Effective amount," for the purposes of the screening assay, is intended to mean an amount that will cause a detectable difference, and preferably a significant difference, in the measured effect as compared to a similar treatment without the candidate inhibitor substance.

Once the candidate inhibitor substance has been provided to a cell that expresses ORF P, the evaluation of the effects of the inhibitor may be undertaken. Depending on the type of assay used, it may be possible to automate this process and test hundreds of candidates at the same time. For example, 96-well trays may be employed in which several wells are reserved for controls while the remainder comprise test substances, usually with each substance being tested at several different amounts.

B. Inducers of ORF P Activity

In another embodiment of the screening assay, one will test candidate substances for the ability to induce or enhance ORF P activity. As stated above, enhancing ORF P activity may make it possible (i) to force HSV into a latent state from an active state, (ii) to prevent latency by curtailing viral infection before the virus can be transported to the neural ganglia and (iii) to prevent reactivation of virus from its latent state. Several different formats exist.

First, like the assay described above regarding inhibitors of ORF P activity, one may examine cells infected with a virus encoding a derepressed ORF P gene with respect to their ability to splice ICP0 and ICP22 transcripts, although later in infection. Monitoring of ICP0 and ICP22 levels during the early phases of infection, both in the presence and absence of a candidate inhibitor, will provide a way of measuring the effect of the candidate, the later phases of infection being less instructive.

Second, one may perform binding studies between ORF P and the various splicing factors which have been identified as targets for ORF P binding, may be examined when combined with ORF P and a candidate inhibitor. These assays may examine the mobility shift, in gel electrophoresis, of either ORF P or the splicing factor, both in the presence and absence of a candidate inducer. Improved binding, in quantity or strength of binding, will indicate an inducer substance.

Third, where the candidate inhibitor is predicted to increase the amount of ORF P expressed, or to limit the processing of ORF P, one may look directly at ORF P in its various forms, including its degree of phosphorylation. The examination of ORF P may be on the basis of immunologic reactivity. Again, as above, this can be accomplished in a variety of ways but, advantageously will be performed via radioimmune precipitation, Western blot or other such routine assay.

Essential amounts of the substance will be determined on the basis of the substances ability to cause a detectable difference, and preferably a significant difference, in the measured effect as compared to a similar treatment without the candidate substance.

VII. Pharmaceuticals and In Vivo Methods for the Treatment of Disease

Aqueous pharmaceutical compositions of the present invention will have an effective amount of an ORF P expression construct, an antisense ORF P expression construct, an expression construct that encodes a therapeutic gene along with an ORF P gene, a protein that inhibits ORF P function, such as an anti-ORF P antibody, or an ORF P polypeptide or any other suitable composition. Such compositions generally will be dissolved or dispersed in a pharmaceutically acceptable carrier or aqueous medium. An "effective amount" for the purposes of therapy, is defined at that amount that causes a clinically measurable difference in the condition of the subject. This amount will vary depending on the substance, the condition of the patient, the type of treatment, the location of the lesion, etc.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-viral agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains glycosylceramide synthesis inhibitory compounds alone or in combination with a chemotherapeutic agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In many cases, the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases. In certain other cases, the formulation will be geared for administration to the central nervous system, e.g., the brain.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

IX. Examples

The following examples are included to demonstrate preferred embodiments of the present invention. It should be appreciated by those of skill in the art that that techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar results without departing from the spirit and scope of the invention.

EXAMPLE 1

Materials and Methods

Cell lines and Viruses. HeLa, SK-N-SH and HEp-2 cell lines were obtained from the American Type Culture Collection, Rockville, Md. HSV-1(F) is the prototype HSV-1 strain used in this laboratory (Ejercito et al., 1968). In the recombinant virus R7530, the ICP4-binding site at the transcription initiation site of ORF P has been ablated by base substitution mutagenesis (Lagunoff et al., 1996).

Plasmids. pRB5105 contains the ORF P domain from amino acid 85 to 248 fused in frame with the DNA-binding-domain of GAL4 in pGBT9 (Clontech, Palo Alto, Calif.). pRB4966 contains the same ORF P domain fused in frame with the glutathione S-transferase (GST) in pGEX4T-1 (Pharmacia, Uppsula, Sweden).

Two-Hybrid-System. pGBT9-ORFP was transformed into yeast strain HF7c (Clontech). Transformants were grown to large-scale (1 liter) and transformed with 0.5 mg of an EBV-transformed human peripheral blood lymphocyte cDNA library in pACT (Clontech). Double-transformants were selected in medium lacking trytophane, leucine and histidine. Colonies were restreaked on the same medium and then tested for LacZ activity by filter-assay, as recommended by the manufacturer. LacZ-positive colonies were grown 24 hrs in medium lacking leucine, and total yeast DNA was extracted and electroporated into E. coli HB101. Bacterial transformants were selected on M9 minimal medium (Sambrook et al., 1989)) containing ampicillin (50μg/ml), proline (40 μg/ml), 1 mM thiamine, 0.4% glucose and an amino acid mixture lacking leucine, as described in the manufacturer'protocol. Mini-preparations of plasmids were made by the alkaline lysis method (Sambrook et al., 1989), retransformed into yeast alone or with various GAL4 DNA-binding domain fusion proteins, and LacZ activity was tested by filter assay.

Purification of the ORF P antibody. The preparation of an antibody to the amino terminal domain of ORF P has been described. The anti-ORF P IgG was purified as follows. One-half ml of serum was loaded on a protein A column (ImmunoPure IgG Purification Kit, Pierce, Rockford, Ill.) and approximately 12 mg IgG were recovered following the procedures recommended by the manufacturer. Of this amount, 3 mg were mixed with 3 mg of GST-ORF P fusion protein coupled to CNBr-activated Sepharose 4B (Pharmacia), and the mixture was incubated for 1.5 hours at 4° C. The beads were rinsed with 10 mM Tris-Cl, pH 7.5 and then with the same buffer but containing 0.5 M NaCl. The antibodies were eluted with 100 mM glycine, pH 2.5 and 100 mM triethylamine, pH 11.5, dialyzed against PBS and stored at −20° C.

Photomicrographs of infected cells. Hep-2, SK-N-SH and HeLa cells were infected with virus R7530 and reacted with antibodies to SC35 alone, to ORF P alone and to both ORF P and SC35. Confluent cells grown on wells on 1×3 inch slides were infected with approximately $10^6$ PFU of virus, incubated at 37° C. and fixed in methanol for 20 min. at −20° C. The cells were reacted for 30 min with PBS containing 20% normal human serum and 1% BSA at room temperature, rinsed once with PBS and reacted overnight at 4° C. with the primary antibody diluted in PBS containing 10% normal human serum and 1% BSA. The final dilutions were 1:40 for anti-ORF P antibody, purified as described in Materials and Methods, and 1:2000 for anti-SC35 antibody (Sigma, St Louis, Mo.). Cells were rinsed three times in PBS and reacted for one hr with goat anti-rabbit IgG conjugated to Texas Red (Molecular Probes Inc., Eugene, Oreg.) or goat anti-mouse IgG conjugated to fluorescein isothiocyanate (FITC, Sigma), rinsed again three times with PBS, mounted in PBS containing 90% glycerol and 1 mg of p-phenylenediamine per ml. The slides were examined under a Zeiss confocal fluorescence microscope, digitized images of the fluorescent antibody stained cells were acquired with software provided with the microscope and printed by a Tektronix 440 phaser printer. Single color images were acquired by excitation using an argon/krypton laser at 488 nm (FITC) or 568 nm (Texas red). Double-stained images were obtained by acquiring a split image of both fluorochromes filtered by 515–540 nm band pass (FITC) and 590 nm long pass (Texas red) filters and subsequent overlaying of the two color images.

Photographic image of cell proteins bound to GST-fusion proteins, electrophoretically separated in denaturing gels and reacted with a human sera to the Sm proteins. Recombinant pGEX vectors were transformed into E.coli BL21 and fusion proteins were isolated from a large-scale culture as recommended by the manufacturer (Pharmacy, Uppsala, Sweden). HeLa cells from a 150 cm² flask were scraped into phosphate buffered saline (PBS), washed with PBS and resuspended in 600 μl of PBS* (1% deoxycholate, 1% NP-40, 10 μm tolylsulfonyl phenylalanyl chloromethyl ketone, and 10 μm α-tosyl-L-lysine chloromethyl ketone in PBS). The cell extract (150 μl) was reacted with 2–5 μg of GST or GST-ORF P proteins bound to glutathione-agarose (Sigma) for 3–4 hours at 4° C. The beads were then collected by low speed centrifugation, washed three times with 1 ml each of PBS, and resuspended in 60 μl of 2X disruption buffer (100 mM Tris-Cl, pH 6.8; 200 mM dithiothreithol; 4% sodium dodecyl sulfate; 0.2% bromphenol blue; 20% glycerol). Proteins were separated in 10% denaturing polyacrylamide gels, transferred to nitrocellulose, blocked, reacted with the human Sm antisera (ANA human serum #5, Centers for Disease Control, Atlanta) and then with a goat anti-human antibody conjugated to alkaline phosphatase, and processed as described by the manufacturer (Biorad, Richmond, Calif.).

Photographic image of infected cell proteins electrophoretically separated in denaturing gels and reacted with antibodies to a proteins. Cells grown in 25 cm² flasks were infected with 10 PFU of virus/cell, incubated for 8 or 18 hrs at 37° C., scraped into PBS and resuspended in 200 μl of 2X SDS-disruption buffer. Approximately 60–100 μl of the cell lysate were electrophoretically separated in 7% denaturing polyacrylamide gels cross-linked with bis-acrylamide, electrically transferred to a nitrocellulose sheet, blocked in 5% skim milk in PBS, reacted with the indicated antibody, then reacted with the secondary goat anti-mouse or anti-rabbit antibody conjugated to alkaline phosphatase and processed for colorimetric detection with alkaline phosphatase.

EXAMPLE 2

Results

ORF P interacts with components of the cellular RNA splicing factors. The domain of the ORF P gene encoding amino acids 85 to 248 (FIG. 1B) was cloned into pGBT9 and transformed into the yeast strain HF7c to yield HF7c/ORFP. Control experiments showed that the product of the chimeric gene did not transactivate the chromosomally located LacZ gene in yeast (data not shown). To screen for interacting proteins, HF7c/ORFP was transformed with a cDNA library from an EBV-transformed human peripheral blood lymphocyte cell line and transformants were selected as described in the Material and Methods. Of approximately 700,000 transformants, nine displayed strong expression of LacZ. The plasmids containing the cDNAs were isolated and retransformed with various fusion proteins. Expression of LacZ could be detected only in presence of the ORF P fusion protein, but not in the presence of irrelevant chimeric genes, such as ICP22, p53 and lamin or by itself (data not shown). The cDNAs were sequenced, and all nine were shown to match completely p32, a subunit of the essential non-snRNP splicing factor SF2/ASF.

Figure 2:
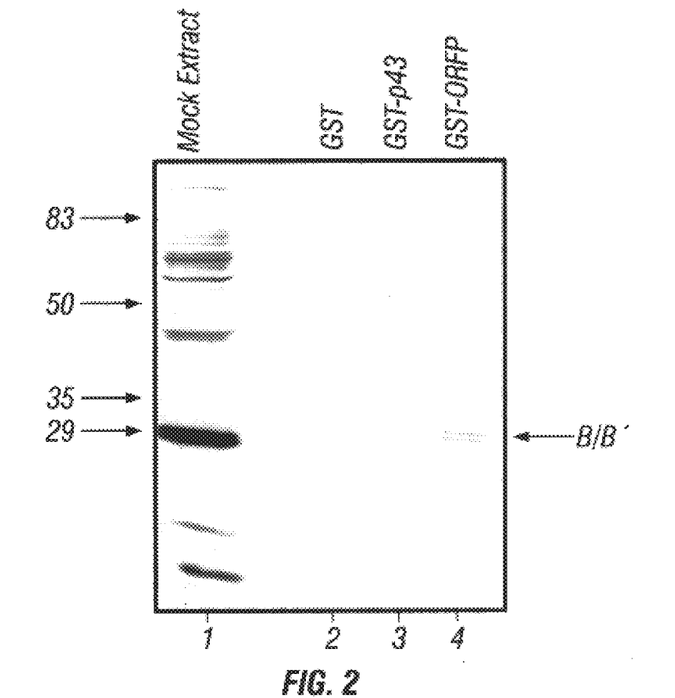
FIG. 2. Photographic image of cell proteins bound to GST-fusion proteins, electrophoretically separated in denaturing gels and reacted with a human sera to the Sm proteins. Recombinant pGEX vectors were transformed into E.coli BL21 and fusion proteins were isolated from a large-scale culture. Molecular weights (in kDa) are shown on the left. Lane 1: cell extract from HeLa cells. Lanes 2,3 and 4: HeLa cell extract bound to GST, GST-p43 and GST-ORF P, respectively. B/B' refers to the position of the B (28 kDa) and B' (29 kDa) polypeptides.

Of the various proteins forming the transcriptional machinery of the cells, antibodies to SC35, a splicing factor belonging to the same superfamily of arginine/serine-rich splicing factors (SR proteins) as SF2/ASF (Fu, 1995), and to the SM antigens, the protein components of the small nuclear ribonucleoproteins (snRNPs; Petersson et al., 1984), were available. To test the reactivity of the ORF P protein with splicing factors, a glutathione-S-transferase (GST) fusion protein to ORF P was made and reacted with cell extract from uninfected HeLa cells and processed for detection of either SC35 or the SM splicing factors by immunoblotting. The ORF P-GST fusion specifically bound the B/B' components of the SM antigens, whereas GST alone or an irrelevant GST fusion did not bind any of the SM proteins (FIG. 2). The same results were obtained with extracts of HSV-infected cells, except that the intensity of the B/B' doublet was weaker, possibly because of a general shutoff of host macromolecular synthesis induced by the HSV-1 infection. Since the SC35 antibodies did not react with denatured antigens, it could not be tested whether the GST-ORF P captured SC35 proteins. The results of the experiment with the anti-SM antibody suggest that ORF P also interacts with that factor.

ORF P and splicing factors colocalize in the nucleus of infected cells. The results described above suggest an interaction between ORF P and components of the splicing machinery. To further verify this interaction, cells were infected with a recombinant virus R7530, in which the ICP4 binding site at the transcription start site of ORF P was mutagenized to derepress the gene. At 18 hrs after infection the cells were fixed, reacted with antibody, and examined by immunofluorescence for the localization of ORF P and the proteins SC35 and SM. The results were that ORF P colocalized with both SC35 and SM. A problem which emerged during the preliminary examination was that the amounts of Texas Red fluorescence indicative of ORF P protein was lower than that of the splicing factors. To insure that fluorescence was not due to spillover, infected cells were reacted with anti-ORF P alone, anti-SC35 alone, or both antibodies. The infected cells were then photographed with the same settings for both Texas Red (ORF P) and FITC (SC35). Only the infected cells reacted with both antibodies showed yellow structures characteristic of co-localization of Texas Red and FITC conjugated antibodies.

Overexpression of ORF P results in a reduction in the level of expression of ICP0 and ICP22. ORF P maps in the genome domain transcribed during latency; it is expressed only in absence of functional ICP4. In the preceding section, it was shown that ORF P colocalizes and interacts with cellular splicing factors. If ORF P plays a role in the establishment of the latent state, one could expect that it would act to down-regulate the expression of α regulatory proteins, which are crucial for the initiation of productive infection. Of the six α genes (α0, α4, α22, α27, α47, and $U_S1.5$) (Roizman and Sears, 1995; Carter and Roizman, 1996), three (α0, α22, and α47) yield spliced mRNAs (FIG. 1A). The 5'-untranslated transcribed domain of α22 and α47 genes are identical and contain identical introns. It would, therefore, be expected that if accumulation of ORF P affects the synthesis of proteins encoded by spliced mRNAs, the effects would be directly demonstrable by examination of the levels of ICP0 and ICP22 in cells infected with wild-type virus and the recombinant R7530, which encodes derepressed ORF P genes. Since ICP27 and ICP4 arise from unspliced mRNAs, they should discriminate between an overall effect on protein synthesis and one which specifically affects the levels of accumulation of proteins encoded by spliced mRNAs.

Figure 3:
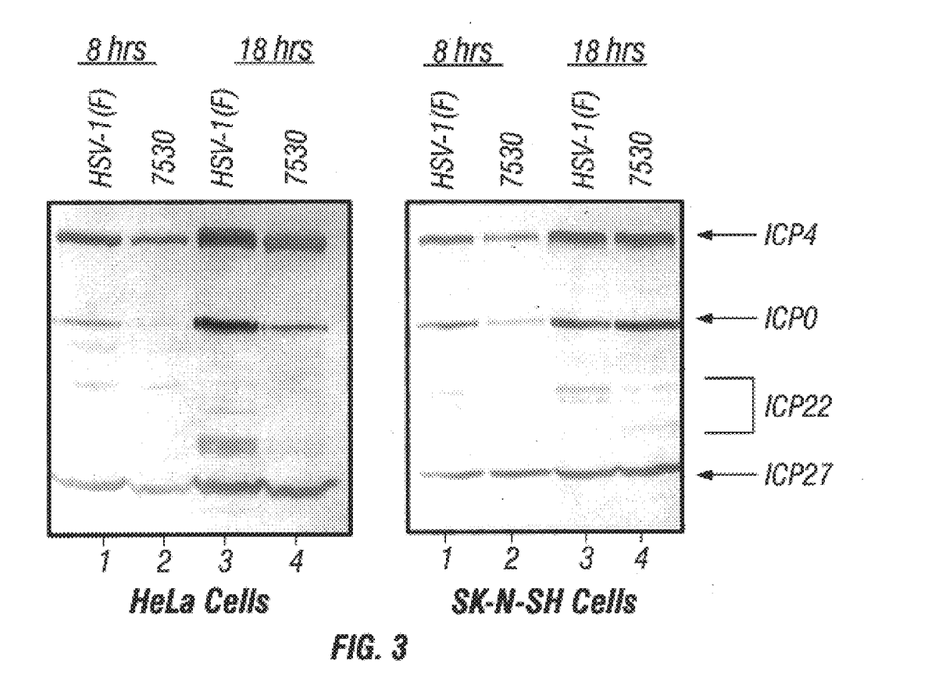
FIG. 3. Photographic image of infected cell proteins electrophoretically separated in denaturing gels and reacted with antibodies to a α proteins. Cells grown in 25 cm² flasks were infected with 10 PFU of virus/cell. Left hand lanes: HeLa cells infected with either HSV-1(F) (lanes 1 and 3) or recombinant R7530 (lanes 2 and 4). Right hand lanes: SK-N-SH cells infected with either HSV-1(F) (lanes 1 and 3) or R7530 (lanes 2 and 4). The antibodies were a rabbit polyclonal antibody R77 to ICP22 and mouse monoclonal antibodies to ICP0 (1083), ICP4 (H640) and ICP27 (H11113) described previously (Ackermann et al., 1984; Ackermann et al., 1985).

The results of such studies on HeLa and SK-N-SH cell lines are shown in FIG. 3. In this series of experiments, the cells were harvested at 8 and 18 hrs after infection, solubilized, subjected to electrophoresis in denaturing polyacrylamide gels, transferred to a nitrocellulose sheet and reacted with antibodies to ICP4, ICP0, ICP22 and ICP27. The results are summmarized as follows. In both HeLa and SK-N-SH cell lines at both 8 and 18 hrs after infection with either virus, the levels of accumulated ICP4 and ICP27 were similar if not identical. At 8 hrs after infection of HeLa cells with the R7530 recombinant virus, the amounts of ICP0 and ICP22 were reduced relative to those of wild-type infected cells. This difference also was apparent at 18 hrs after infection. In SK-N-SH cells at 18 hrs after infection with the R7530 virus, the levels of ICP0 were nearly identical to those seen in wild-type infected cells, whereas the level of ICP22 was still reduced relative to that of wild-type infected cells. These results suggest that ORF P exerts its activity through the host splicing machinery.

Figure 4:
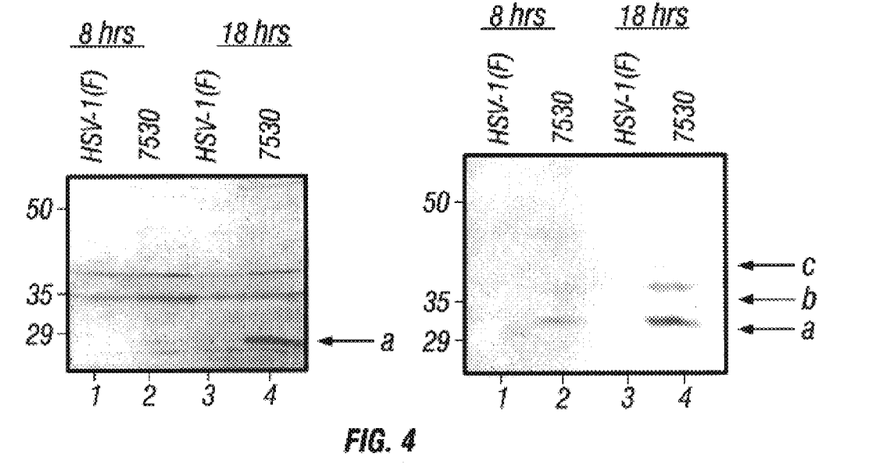
FIGS. 4A–B. Photographic image of infected cell proteins electrophoretically separated and reacted with an antibody to ORF P. HeLa cells (FIG. 4A) and SK-N-SH cells (FIG. 4B) were infected with HSV-1(F) (lanes 1 and 3) or with R7530 (lanes 2 and 4), harvested after 8 hours (lanes 1 and 2) and 18 hours (lanes 3 and 4), electrophoretically separated, transferred to nitrocellulose and reacted with an antibody to ORF P. The different forms of ORF P are designated by the letters on the right. Numbers on the left are molecular weight markers (X 1000).

The extent of posttranslational modification of ORF P varies significantly in different cell lines and correlates with ORF P activity. The results described so far suggest that the activity of ORF P is regulated differently in the two cell lines. In an earlier report, the inventors' laboratory showed that ORF P is extensively modified late in infection and suggested that these modifications could be a mechanism by which the activity of ORF P could be modulated (Lagunoff & Roizman, 1995). To test if the phenotypes observed in the two different cell lines could be correlated to the extent of ORF P modification, lysates of infected HeLa or of SK-N-SH cells were solubilized, electrophoretically separated in denaturing gels, transferred to a nitrocellulose sheet and probed with anti-ORF P antibody. The results, showing in FIG. 4, demonstrate that ORF P was barely detectable in HeLa cell extracts at 8 hrs after infection. At 18 hrs after infection, only the unmodified form of ORF P (ORF Pa) was detectable in these cells (FIG. 4A, lane 4). In SK-N-SH cells, only the nascent form of ORF P (ORF Pa) was detected at 8 hrs. after infection. At 18 hrs, however, the lysates of SK-N-SH cells contained multiple forms of ORF P, including the slower migrating ORF Pb and ORF Pc (FIG. 4B; compare lanes 2 and 4). ORF P was not detected in lysates of cells infected with the wild type virus (FIG. 4A, lanes 1 and 3; FIG. 4B, lanes 1 and 3).

X. References

The following references, to the extent that they provide exemplary procedural details or other information supplementary to that set forth herein, are incorporated by reference:

Ackermann et al., *J. Virol.* 52:108–118, 1984.
Ackermann et al., *J. Virol.* 56:207–215, 1985.
Baichwal & Sugden, In: *GENE TRANSFER* Kucherlapati, R., ed. New York: Plenum Press, pp. 117–148, 1986.
Batterson & Roizman, *J. Virol.*, 46:371–377, 1983.
Benvenisty & Neshif, *Proc. Nat'l Acad. Sci. USA* 83:9551–9555, 1986.
Bittner et al., *Methods in Enzymol.*, 153:516–544, 1987.
Boussif et al., "A versatile vector for gene and oligonucleotide transfer into cells in culture and in vivo: Polyethylenimine," *Proc. Natl. Acad. Sci. USA*, 92:7297–7301, 1995.
Brutlag et al., *CABIOS*, 6:237–245, 1990.
Cáceres et al., *Science*, 265:1706–1709, 1994.
Campbell et al., *J. Mol. Biol.*, 180:1–19, 1984.
Carter and Roizman, *J. Virol.* 70, 172–178, 1996.
Chen & Okayama, *Mol. Cell Biol.*, 7:2745–2752, 1987.
Chou & Fasman, *Adv. Enzymol. Relat. Areas Mol. Biol.* 47:45–148, 1978a.
Chou & Fasman, *Ann. Rev. Biochem.* 47:251–276, 1978b.
Chou & Fasman, *Biochemistry*, 13(2):211–222, 1974b.
Chou & Fasman, *Biochemistry*, 13(2):222–245, 1974a.
Chou & Fasman, *Biophys. J.*, 26:367–384, 1979.
DeLuca et al., *J. Virol.*, 56:558–570, 1985.
Dubensky et al., *Proc. Nat'l Acad. Sci. USA*, 81:7529–7533, 1984.
Ejercito et al., *J. Gen Virol.*, 2:357–364, 1968.
Fechheimer et al., *Proc. Nat'l Acad. Sci. USA*, 84:8463–8467, 1987.
Ferkol et al., *FASEB J.*, 7:1081–1091, 1993.
Fetrow & Bryant, *Biotechnology*, 11:479–483, 1993.
Fraley et al., *Proc. Nat'l Acad. Sci. USA*, 76:3348–3352, 1979.
Fu, X., *RNA*, 1:663–680, 1995.

Ghosh & Bachhawat, In: Wu G. and C. Wu ed. Liver diseases, targeted diagnosis and therapy using specific receptors and ligands. New York: Marcel Dekker, pp. 87–104, 1991.
Glorioso et al., *Ann. Rev. Microbiol.* 49:675–710, 1995.
Gopal, *Mol. Cell Biol.,* 5:1188–1190, 1985.
Graham & Van Der Eb, *Virology,* 52:456–467, 1973.
Harland & Weintraub, *J. Cell Biol.,* 101:1094–1099, 1985.
Holland et al., *Virology,* 101:10–18, 1980.
Honess & Roizman, *J. Virol.,* 14:8–19, 1974.
Honess & Roizman, *J. Virol.,* 16:1308–1326, 1975.
Jameson & Wolf, *Comput. Appl. Biosci.,* 4(1):181–186, 1988.
Johnson et al., *BIOTECHNOLOGY AND PHARMACY,* Pezzuto et al., eds., Chapman and Hall, New York, 1993.
Kaneda et al., *Science,* 243:375–378, 1989.
Kanopka et al., *Nature,* 381:535–538, 1996.
Kato et al., *J. Biol. Chem.,* 266:3361–3364, 1991.
Klein et al., *Nature,* 327:70–73, 1987.
Kyte & Doolittle, *J. Mol. Biol.,* 157(1):105–132, 1982.
Lagunoff et al., *J. Virol.,* 70:1810–1817, 1996.
Lagunoff et al., *J. Virol.,* 69:3615–3623, 1995.
McNally and McNally, *J. Virol.,* 701163–1172, 1996.
Nicolas & Rubenstein, In: *Vectors: A survey of molecular cloning vectors and their uses,* Rodriguez & Denhardt (eds.), Stoneham: Butterworth, pp. 494–513, 1988.
Nicolau & Sene, *Biochem. Biophys. Acta,* 721:185–190, 1982.
Nicolau et al., *Methods Enzymol.,* 149:157–176, 1987.
Perales et al., *Proc. Nat'l Acad. Sci. USA,* 91:4086–4090, 1994.
Pettersson et al., *J. Biol. Chem.,* 259:5907–5914, 1984.
Post et al., *Cell* 24:555–565, 1981.
Potter et al., *Proc. Nat'l Acad. Sci. USA,* 81:7161–7165, 1984.
Ridgeway, In: Rodriguez R L, Denhardt D T, ed. Vectors: A survey of molecular cloning vectors and their uses, Stoneham: Butterworth, pp.467–492, 1988.
Rippe et al., *Mol. Cell Biol.,* 10:689–695, 1990.
Roizman & Sears, In *Fields' Virology,* 3rd Edition, eds. Fields, et al. (Raven Press, New York, N.Y.), pp. 2231–2295, 1995.
Sambrook et al., *Molecular Cloning. A Laboratory Manual,* (Cold Spring Harbor Laboratory Press), 2nd Ed., 1989.
Temin, In: *Gene Transfer,* Kucherlapati (ed.), New York: Plenum Press, pp. 149–188, 1986.
Tur-Kaspa et al., *Mol. Cell Biol.,* 6:716–718, 1986.
Wagner et al., *Science,* 260:1510–1513, 1993.
Wang and Manley, *RNA,* 1:335–346, 1995.
Ward and Roizman, *Trends Genet.,* 10: 267–274, 1994.
Weinberger et al., *Science,* 228:740–742, 1985.
Wolf et al., *Comput. Appl. Biosci.,* 4(1):187–191, 1988.
Wong et al., *Gene,* 10:87–94, 1980.
Wu & Wu, *Adv. Drug Delivery Rev.,* 12:159–167, 1993.
Wu & Wu, *Biochemistry,* 27:887–892, 1988.
Wu & Wu, *J. Biol. Chem,* 262:4429–4432, 1987.
Yang et al., *Proc. Nat'l Acad. Sci. USA,* 87:9568–9572, 1990.
Zelenin et al., *FEBS Lett.,* 280:94–96, 1991.
U.S. Ser. No.08/438,415

What is claimed is:

1. A method for inducing latency in a herpesvirus infected cell in vitro comprising the step of increasing the level of ORF P polypeptide in said cell, wherein ORF P is expressed at a level sufficient to induce latency in said herpesvirus infected cell.

2. The method of claim 1, wherein said herpesvirus is a herpes simplex virus.

3. The method of claim 2, wherein said herpesvirus is a type I herpes simplex virus.

4. The method of claim 2, wherein said herpesvirus is a type II herpes simplex virus.

5. The method of claim 1, wherein said cell is a human cell.

6. The method of claim 1, wherein said increasing comprises providing the ORF P polypeptide to said cell.

7. The method of claim 6, wherein said providing comprises contacting said cell with the ORF P polypeptide.

8. The method of claim 6, wherein said providing comprises introducing into said cell a nucleic acid encoding the ORP P polypeptide.

9. The method of claim 8, wherein said nucleic acid is under the transcriptional control of a promoter active in eukaryotic cells.

10. The method of claim 9, wherein said promoter is a herpesvirus promoter.

11. The method of claim 10, wherein said introduction is performed using a replication-deficient vector comprising said nucleic acid.

12. The method of claim 11, wherein said vector is a herpesvirus vector.

13. The method of claim 12, wherein said herpesvirus vector is contained in an infectious herpesvirus particle and said contacting is under conditions that permit infection of said cell by said herpesvirus particle.

14. The method of claim 13, further comprising a step of administering an anti-viral agent to said cell.

* * * * *

SEQUENCE LISTING

```
<160> NUMBER OF SEQ ID NOS: 2

<210> SEQ ID NO 1
<211> LENGTH: 223
<212> TYPE: PRT
<213> ORGANISM: HERPES VIRUS, TYPE 1
<220> FEATURE:
<221> NAME/KEY: UNSURE
<222> LOCATION: (97)
<223> OTHER INFORMATION: Xaa = Any Set Containing N
<221> NAME/KEY: UNSURE
<222> LOCATION: (176)
<223> OTHER INFORMATION: Xaa = Any Set Containing N

<400> SEQUENCE: 1

Met Thr Ala Ser Ala Ser Ala Thr Arg Arg Arg Asn Arg Ala Arg Ser
 1               5                  10                  15

Ala Arg Ser Arg Ala His Glu Pro Arg Arg Ala Arg Arg Ala Ala Glu
                20                  25                  30

Ala Gln Thr Thr Arg Trp Arg Thr Arg Thr Trp Gly Glu Lys Arg Thr
            35                  40                  45

Arg Ala Gly Val Ala Gly Gly Ser Gly Ala Pro Ser Pro Pro Ala Arg
        50                  55                  60

Arg Arg Arg Arg Arg Ala Arg Cys Ser Ala Val Thr Arg Arg Arg Arg
65                  70                  75                  80

Ala Arg Arg Gly Gly Arg Arg Lys Gly Arg Glu Gly Gly Trp Glu Gly
                85                  90                  95

Xaa Ala Pro Pro Pro Gly Pro Ala Pro Gly Gly Gly Asp Arg Gly Arg
            100                 105                 110
```

Gly Ala Ala Ala Val Gly Arg Ala Ser Gly Ala Ser Gly Gly Gly
            115                 120                 125

Leu Ser Gly Gln Ser Ser Ser Ser Ser Ser Asp Ala Asp Ser Gly
            130                 135                 140

Thr Trp Ser His Trp Arg Ser Ser Glu Gln Glu Gly Gly Gly Pro
145                 150                 155                 160

Pro Ala Gly Gly Gly Gly Ala Ala Gly Ala Leu Leu Thr Xaa
            165                 170                 175

Gly Ser Glu Leu Gly Val Glu Val Thr Trp Asp Cys Ala Val Gly Thr
            180                 185                 190

Ala Pro Val Gly Pro Gly Gly Arg Gly Arg Gly Pro Arg Trp Arg
            195                 200                 205

Arg Arg Arg Ala Met Glu Thr Glu Ser Val Pro Gly Trp Pro
210                 215                 220

<210> SEQ ID NO 2
<211> LENGTH: 226
<212> TYPE: PRT
<213> ORGANISM: HERPES VIRUS, TYPE 1
<220> FEATURE:
<221> NAME/KEY: UNSURE
<222> LOCATION: (100)..(179)
<223> OTHER INFORMATION: xAA = Any Set Containing NN

<400> SEQUENCE: 2

Met Thr Ala Ser Ala Ser Ala Thr Arg Arg Asn Arg Ala Arg Ser
1               5                   10                  15

Ala Arg Ser Arg Ala His Glu Pro Arg Arg Ala Arg Ala Ala Glu
            20                  25                  30

Ala Gln Thr Thr Arg Trp Arg Thr Arg Thr Trp Gly Glu Lys Arg Thr
            35                  40                  45

Arg Ala Gly Val Ala Gly Val Ala Gly Gly Ser Gly Ala Pro Ser Pro
50                  55                  60

Pro Ala Arg Arg Arg Arg Arg Ala Arg Cys Ser Ala Val Thr Arg
65                  70                  75                  80

Arg Arg Arg Ala Arg Arg Gly Gly Arg Lys Gly Arg Glu Gly Gly
            85                  90                  95

Trp Glu Gly Xaa Ala Pro Pro Pro Gly Pro Ala Pro Gly Gly Gly Asp
            100                 105                 110

Arg Gly Arg Gly Ala Ala Ala Val Gly Arg Ala Ser Gly Ala Gly Ser
            115                 120                 125

Gly Gly Gly Leu Ser Gly Gln Ser Ser Ser Ser Ser Ser Asp Ala
            130                 135                 140

Asp Ser Gly Thr Trp Ser His Trp Arg Ser Ser Glu Gln Glu Gly
145                 150                 155                 160

Gly Gly Pro Pro Ala Gly Gly Gly Gly Ala Ala Ala Gly Ala Leu
            165                 170                 175

Leu Thr Xaa Gly Ser Glu Leu Gly Val Glu Val Thr Trp Asp Cys Ala
            180                 185                 190

Val Gly Thr Ala Pro Val Gly Pro Gly Gly Arg Gly Arg Gly Pro
            195                 200                 205

Arg Trp Arg Arg Arg Arg Arg Ala Met Glu Thr Glu Ser Val Pro Gly
            210                 215                 220

Trp Pro
225